(12) United States Patent
Enomoto et al.

(10) Patent No.: US 9,633,480 B2
(45) Date of Patent: Apr. 25, 2017

(54) RADIOGRAPHIC IMAGE ANALYZING DEVICE, METHOD, AND RECORDING MEDIUM

(71) Applicant: FUJIFILM Corporation, Tokyo (JP)

(72) Inventors: Jun Enomoto, Ashigarakami-gun (JP); Yasufumi Oda, Ashigarakami-gun (JP); Takashi Tajima, Ashigarakami-gun (JP); Takeshi Kuwabara, Ashigarakami-gun (JP); Daiki Harada, Ashigarakami-gun (JP); Yuichi Hosoi, Ashigarakami-gun (JP); Haruyasu Nakatsugawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 35 days.

(21) Appl. No.: 14/855,540

(22) Filed: Sep. 16, 2015

(65) Prior Publication Data

US 2016/0086328 A1    Mar. 24, 2016

(30) Foreign Application Priority Data

Sep. 24, 2014   (JP) .................................. 2014-193994

(51) Int. Cl.
   *G06T 7/60*   (2006.01)
   *A61B 6/00*   (2006.01)
   (Continued)

(52) U.S. Cl.
   CPC .......... *G06T 19/006* (2013.01); *A61B 6/5211* (2013.01); *A61B 6/5282* (2013.01);
   (Continued)

(58) Field of Classification Search
   CPC ....... G06T 7/602; G06T 11/60; G06T 19/006; G06T 2207/10116; G06T 2207/30061; A61B 6/5211; A61B 6/5282
   See application file for complete search history.

(56) References Cited

U.S. PATENT DOCUMENTS

| | | | |
|---|---|---|---|
| 7,269,246 B2* | 9/2007 | Ohishi | A61B 6/504 378/196 |
| 2001/0012330 A1* | 8/2001 | Ogura | A61B 6/06 378/95 |

(Continued)

FOREIGN PATENT DOCUMENTS

| | | | |
|---|---|---|---|
| JP | 2-244881 A | | 9/1990 |
| JP | H0614911 | * | 1/1994 |

(Continued)

OTHER PUBLICATIONS

Boone et al., "An analytical model of the scattered radiation distribution in diagnostic radiology", 1988, Medical Physics, vol. 15, Issue 5, 721-725.*

(Continued)

*Primary Examiner* — Katrina Fujita
(74) *Attorney, Agent, or Firm* — Birch, Stewart, Kolasch & Birch, LLP

(57) ABSTRACT

An image obtaining unit obtains a subject image, a body thickness distribution modifying unit receives input of a virtual model having an estimated body thickness distribution and modifies the estimated body thickness distribution of the virtual model to output the modified estimated body thickness distribution, and a body thickness distribution determining unit determines the outputted estimated body thickness distribution to be used as the body thickness distribution of the subject. The body thickness distribution determining unit includes a judging unit for switching, according to a judgment condition, between a first control under which the body thickness distribution modifying process is iteratively executed until a first termination condition is satisfied and a second control under which the body thickness distribution modifying process is iteratively executed until a second termination condition that is differ- (Continued)

ent from the first termination condition is satisfied so that the first control or the second control is executed.

12 Claims, 5 Drawing Sheets

(51) Int. Cl.
  *G06T 19/00* (2011.01)
  *G06T 11/60* (2006.01)
(52) U.S. Cl.
  CPC .............. *G06T 7/602* (2013.01); *G06T 11/60* (2013.01); *G06T 2207/10116* (2013.01); *G06T 2207/30061* (2013.01)

(56) References Cited

U.S. PATENT DOCUMENTS

| | | | | |
|---|---|---|---|---|
| 2004/0125921 | A1* | 7/2004 | Allouche | A61B 6/544 378/207 |
| 2005/0169425 | A1* | 8/2005 | Takasawa | A61B 6/00 378/97 |
| 2011/0075793 | A1* | 3/2011 | Akahori | A61B 6/032 378/8 |
| 2013/0089176 | A1* | 4/2013 | Nabatame | G01N 23/046 378/8 |
| 2014/0119509 | A1* | 5/2014 | Kaneko | A61B 6/4233 378/62 |
| 2014/0341350 | A1* | 11/2014 | Muroi | A61B 6/463 378/62 |
| 2015/0063526 | A1* | 3/2015 | Kobayashi | G06T 11/005 378/4 |
| 2015/0071414 | A1* | 3/2015 | Oda | H04N 5/32 378/207 |
| 2015/0245807 | A1* | 9/2015 | Tajima | A61B 6/563 378/98 |
| 2015/0251018 | A1* | 9/2015 | Tajima | G06T 5/002 378/28 |
| 2016/0081648 | A1* | 3/2016 | Tajima | A61B 6/5282 378/165 |
| 2016/0140720 | A1* | 5/2016 | Naito | A61B 6/4291 382/132 |
| 2016/0140721 | A1* | 5/2016 | Kawamura | A61B 6/466 382/132 |

FOREIGN PATENT DOCUMENTS

| | | | |
|---|---|---|---|
| JP | 8-266529 A | | 10/1996 |
| JP | 9-24039 A | | 1/1997 |
| JP | 2008000190 | * | 1/2008 |
| JP | 2008011894 | * | 1/2008 |
| JP | 2008246022 | * | 10/2008 |
| JP | 2010005032 | * | 1/2010 |
| JP | 2011104103 | * | 6/2011 |
| JP | 2011135990 | * | 7/2011 |
| JP | 2012020009 | * | 2/2012 |

OTHER PUBLICATIONS

Fivez et al., "Multi-resolution contrast amplification in digital radiography with compensation for scattered radiation", 1996 Proceedings., International Conference on Image Processing, 339-342.*

Ween et al., "Pediatric digital chest radiography, comparison of grid versus non-grid techniques", 2009, European Journal of Radiography, vol. 1, Issue 4, 201-206.*

H. Kato, "A New Method for Eliminating Scatter Components from a Digital X-ray Image by Later Processing", Journal of Japanese Society of Radiological Technology, vol. 62, No. 9, pp. 1359-1368, 2006.

Trotter et al. "Thickness-dependent Scatter Correction Algorithm for Digital Mammography", Proc. SPIE, vol. 4682, pp. 469-478, 2002.

\* cited by examiner

RADIOGRAPHIC IMAGE ANALYZING DEVICE, METHOD, AND RECORDING MEDIUM

CROSS-REFERENCE TO RELATED APPLICATIONS

The present application claims priority under 35 U.S.C. §119 to Japanese Patent Application No. 2014-193994, filed on Sep. 24, 2014. The above application is hereby expressly incorporated by reference, in its entirety, into the present application.

BACKGROUND

The present disclosure relates to a radiographic image analyzing device, a radiographic image analyzing method, and a radiographic image analyzing program for analyzing a radiographic image obtained by imaging a subject, and in particular to a radiographic image analyzing device, a radiographic image analyzing method, and a radiographic image analyzing program for analyzing a radiographic image obtained by imaging a subject to estimate the thickness of the subject at each position on the radiographic image.

It is conventionally known that, when a radiographic image of a subject is taken with radiation transmitted through the subject, image quality of the obtained radiographic image varies due to influences of scattering of the radiation in the subject, lowered transmittance of the radiation, etc., which influences are larger when the thickness of the subject is larger. To address this problem, techniques have been proposed to roughly estimate the thickness of the subject based on imaging conditions and various information, such as signal values of the radiographic image, the histogram width of signal values of the radiographic image, the length of the subject in the subject image in a predetermined direction, etc., and to change an image processing condition, such as scattered ray removal, performed on the obtained radiographic image or an imaging condition applied to radiographic imaging depending on the estimated thickness of the subject.

For example, a technique disclosed in Japanese Unexamined Patent Publication No. 2(1990)-244881 (hereinafter, Patent Document 1) involves: measuring pixel values of images obtained by radiographic imaging of a simulation subject having known thicknesses under known imaging conditions to prepare a lookup table that associates body thicknesses with pixel values; estimating a schematic body thickness distribution from pixel values of a subject image based on the lookup table; estimating a scattered ray component in the subject image based on the body thickness distribution of the subject image; and obtaining a processed image by subtracting the scattered ray component from the subject image.

D. E. G Trotter et. al., "Thickness-dependent Scatter Correction Algorithm for Digital Mammography", Proc. SPIE, Vol. 4682, pp. 469-478, 2002, (hereinafter, Non-Patent Document 1) discloses a technique to estimate and remove a scattered ray component in a radiographic image based on the body thickness distribution of a human body. According to the image processing method of Non-Patent Document 1, a predetermined function is applied to an inputted subject image based on a body thickness distribution estimated from pixel values of the subject image to generate an estimated scattered ray image, which is an estimate of an image of scattered rays included in the subject image, and the estimated scattered ray image is subtracted from the subject image to generate an estimated primary ray image, which is an estimate of a primary ray image, from the inputted subject image. Then, operations to generate a new estimated scattered ray image by applying the predetermined function to the generated estimated primary ray image, and to generate a new estimated primary ray image by subtracting the new estimated scattered ray image from the subject image are iteratively performed until a certain convergence condition is satisfied to calculate a converged estimated scattered ray image, and the converged estimated scattered ray image is subtracted from the subject image to thereby obtain a processed image from which the scattered ray component is removed. Non-Patent Document 1 also disclose a method for adjusting the predetermined function used to estimate the image of scattered rays included in the subject image based on the body thickness.

SUMMARY

In order to obtain detailed body thicknesses that reflect internal structures of the subject, such as the lung fields in the subject, it is preferred to calculate the thicknesses of the subject based on pixel values of a subject image that is obtained by actually imaging the subject. However, the subject image includes a component of primary rays (a primary ray component) that are transmitted through the subject and directly applied to the radiation detector, and a component of scattered rays (a scattered ray component) of the radiation scattered in the subject.

Therefore, if the method to estimate body thicknesses based on pixel values, as taught in Patent Document 1 or Non-Patent Document 1, is applied to a radiographic image that is taken without using a scattered ray removal grid (or a grid), it is difficult to accurately estimate the body thickness distribution of the subject due to influence of the scattered ray component included in the radiographic image. One may consider taking a subject image using the grid to avoid influence of the scattered ray component. However, for reducing a burden, such as radiation exposure, imposed on the subject, it is demanded to achieve accurate estimation of the body thickness distribution from a subject image that is taken without using the grid.

To meet the above-described demand, the present applicant has proposed a technique, which includes: based on a virtual model set in advance, estimating a primary ray image and a scattered ray image that would be obtained by radiographic imaging of the virtual model; generating an image by combining the estimated primary ray image and the estimated scattered ray image as an estimated image, which is an estimate of a radiographic image that would be obtained by radiographic imaging of a subject; and iteratively modifying a body thickness distribution such that the difference between the generated estimated image and a subject image that is obtained by actual radiographic imaging of the subject is reduced, to thereby accurately calculate the body thickness distribution (see Japanese Patent Application No. 2013-229941).

Further, there are demands from the medical sites not only for obtaining an accurate body thickness distribution by achieving a body thickness distribution estimating process which estimates the body thickness distribution with accuracy as high as possible, but also for keeping the run time of the body thickness distribution estimating process within an acceptable range depending on the purpose of diagnosis of the subject image, the performance of the image analyzing device used, circumstances in the imaging environment, etc., while ensuring high accuracy of the body thickness distribution estimating process.

In view of the above-described circumstances, the present disclosure is directed to accomplishing a radiographic image analyzing device, a radiographic image analyzing method, and a radiographic image analyzing program for analyzing a radiographic image obtained by imaging a subject and estimating a thickness of the subject at each position on the radiographic image, which allow keeping the run time of the body thickness distribution estimating process within an acceptable range while ensuring high accuracy of the body thickness distribution estimating process.

An aspect of the radiographic image analyzing device according to the disclosure is a radiographic image analyzing device for analyzing a subject image obtained by radiographic imaging of a subject to estimate a body thickness distribution of the subject, the device comprising:

an image obtaining unit for obtaining the subject image;
a body thickness distribution modifying unit for receiving input of a virtual model having an estimated body thickness distribution and modifying the estimated body thickness distribution of the virtual model to output the modified estimated body thickness distribution, the body thickness distribution modifying unit comprising:
a virtual model obtaining unit for obtaining the inputted virtual model having the estimated body thickness distribution,
an estimated image generating unit for generating an estimated image, which is an estimate of a radiographic image that would be obtained by radiographic imaging of the subject, by combining an estimated primary ray image, which is an estimate of a primary ray image that would be obtained by radiographic imaging of the obtained virtual model, and an estimated scattered ray image, which is an estimate of a scattered ray image that would be obtained by radiographic imaging of the virtual model, and
a modifying unit for modifying the obtained estimated body thickness distribution such that a difference between the estimated image and the subject image is reduced, and outputting the modified estimated body thickness distribution; and
a body thickness distribution determining unit for controlling execution of a body thickness distribution modifying process that causes the modifying unit to modify the estimated body thickness distribution of the virtual model and output the modified estimated body thickness distribution, causes the virtual model obtaining unit to obtain the virtual model having the outputted estimated body thickness distribution inputted thereto, and causes the estimated image generating unit to generate the estimated image from the virtual model, wherein the body thickness distribution modifying process is iteratively executed until a termination condition is satisfied, and, if the termination condition is satisfied, the body thickness distribution determining unit determines the estimated body thickness distribution that is outputted by the body thickness distribution modifying process when the termination condition is satisfied to be used as the body thickness distribution of the subject,
wherein the body thickness distribution determining unit comprises a judging unit for switching, according to a judgment condition, between a first control under which the body thickness distribution modifying process is iteratively executed until a first termination condition is satisfied and a second control under which the body thickness distribution modifying process is iteratively executed until a second termination condition that is different from the first termination condition is satisfied so that one of the first control and the second control is executed, the number of iterations of the body thickness distribution modifying process under the second control being smaller than the number of iterations of the body thickness distribution modifying process under the first control.

An aspect of the radiographic image analyzing method according to the disclosure is a radiographic image analyzing method to be executed by a radiographic image analyzing device for analyzing a subject image obtained by radiographic imaging of a subject to estimate a body thickness distribution of the subject, the method comprising:

an image obtaining step of obtaining the subject image;
a body thickness distribution modifying step of receiving input of a virtual model having an estimated body thickness distribution and modifying the estimated body thickness distribution of the virtual model to output the modified estimated body thickness distribution, the body thickness distribution modifying step comprising:
a virtual model obtaining step of obtaining the inputted virtual model having the estimated body thickness distribution,
an estimated image generating step of generating an estimated image, which is an estimate of a radiographic image that would be obtained by radiographic imaging of the subject, by combining an estimated primary ray image, which is an estimate of a primary ray image that would be obtained by radiographic imaging of the obtained virtual model, and an estimated scattered ray image, which is an estimate of a scattered ray image that would be obtained by radiographic imaging of the virtual model, and
a modifying step of modifying the obtained estimated body thickness distribution such that a difference between the estimated image and the subject image is reduced, and outputting the modified estimated body thickness distribution; and
a body thickness distribution determining step of controlling execution of a body thickness distribution modifying process that causes the estimated body thickness distribution of the virtual model to be modified and the modified estimated body thickness distribution to be outputted in the modifying step, causes the virtual model having the outputted estimated body thickness distribution to be obtained in the virtual model obtaining step, and causes the estimated image to be generated from the virtual model in the estimated image generating step, wherein the body thickness distribution modifying process is iteratively executed until a termination condition is satisfied, and, if the termination condition is satisfied, the estimated body thickness distribution that is outputted by the body thickness distribution modifying process when the termination condition is satisfied is determined to be used as the body thickness distribution of the subject,
wherein the body thickness distribution determining step comprises a judging step of switching, according to a judgment condition, between a first control under which the body thickness distribution modifying process is iteratively executed until a first termination condition is satisfied and a second control under which the body thickness distribution modifying process is iteratively executed until a second termination condition that is different from the first termination condition is satisfied so that one of the first control and the second control is executed, the number of iterations of the body thickness distribution modifying process under the second control being smaller than the number of iterations of the body thickness distribution modifying process under the first control.

An aspect of the radiographic image analyzing program according to the disclosure is provided in the form of a non-transitory computer-readable recording medium containing a radiographic image analyzing program for analyzing a subject image obtained by radiographic imaging of a subject to estimate a body thickness distribution of the subject, the program causing a computer to function as:

an image obtaining unit for obtaining the subject image;
a body thickness distribution modifying unit for receiving input of a virtual model having an estimated body thickness distribution and modifying the estimated body thickness distribution of the virtual model to output the modified estimated body thickness distribution, the body thickness distribution modifying unit comprising:
a virtual model obtaining unit for obtaining the inputted virtual model having the estimated body thickness distribution,
an estimated image generating unit for generating an estimated image, which is an estimate of a radiographic image that would be obtained by radiographic imaging of the subject, by combining an estimated primary ray image, which is an estimate of a primary ray image that would be obtained by radiographic imaging of the obtained virtual model, and an estimated scattered ray image, which is an estimate of a scattered ray image that would be obtained by radiographic imaging of the virtual model, and
a modifying unit for modifying the obtained estimated body thickness distribution such that a difference between the estimated image and the subject image is reduced, and outputting the modified estimated body thickness distribution; and
a body thickness distribution determining unit for controlling execution of a body thickness distribution modifying process that causes the modifying unit to modify the estimated body thickness distribution of the virtual model and output the modified estimated body thickness distribution, causes the virtual model obtaining unit to obtain the virtual model having the outputted estimated body thickness distribution inputted thereto, and causes the estimated image generating unit to generate the estimated image from the virtual model, wherein the body thickness distribution modifying process is iteratively executed until a termination condition is satisfied, and, if the termination condition is satisfied, the body thickness distribution determining unit determines the estimated body thickness distribution that is outputted by the body thickness distribution modifying process when the termination condition is satisfied to be used as the body thickness distribution of the subject,
wherein the body thickness distribution determining unit comprises a judging unit for switching, according to a judgment condition, between a first control under which the body thickness distribution modifying process is iteratively executed until a first termination condition is satisfied and a second control under which the body thickness distribution modifying process is iteratively executed until a second termination condition that is different from the first termination condition is satisfied so that one of the first control and the second control is executed, the number of iterations of the body thickness distribution modifying process under the second control being smaller than the number of iterations of the body thickness distribution modifying process under the first control.

The "body thickness" as used herein refers to a total thickness of the subject region except an air region present along a traveling path of the applied radiation. For example, the body thickness refers to a total thickness of the subject tissues except air regions, such as air regions in the lung, in the subject present along a traveling path of the applied radiation.

The "estimated image" as used herein may be any image that can substantially be regarded as an image obtained by combining an estimated primary ray image, which is an estimate from the virtual model of a primary ray image that would be obtained by radiographic imaging of the virtual model, and an estimated scattered ray image, which is an estimate from the virtual model of a scattered ray image that would be obtained by radiographic imaging of the virtual model. For example, the estimated primary ray image may be generated by applying a function for generating the estimated primary ray image to the virtual model, and the estimated scattered ray image may be separately generated by applying a function for generating the estimated scattered ray image to the virtual model, and then the estimated primary ray image and the estimated scattered ray image may be combined. Alternatively, the estimated image may be estimated by applying a function for generating the estimated image to the virtual model.

The "difference between the estimated image and the subject image" as used herein refers to the level of correlation between pixel values at corresponding positions on the estimated image and the subject image. The description "the difference between the subject image and the estimated image is reduced" as used herein refers to increasing the correlation between pixel values at corresponding positions on the estimated image and the subject image (i.e., increasing similarity between the images).

In the radiographic image analyzing device according to the disclosure, the judging unit may estimate an estimated run time, which is an estimate of a sum of run times of the body thickness distribution modifying process that is iteratively executed until the first termination condition is satisfied, based on time-series transition of the difference between the estimated image and the subject image during the iteratively executed body thickness distribution modifying process, and the judging unit executes the second control if the estimated run time is greater than a first time limit, and executes the first control if the estimated run time is not greater than the first time limit.

In the radiographic image analyzing device according to the disclosure, the judging unit may execute, based on processing capacity information that indicates processing capacity of the radiographic image analyzing device, the second control if the processing capacity is lower than a certain processing level, and may execute the first control if the processing capacity is not lower than the certain processing level.

The "processing capacity information indicating processing capacity of the radiographic image analyzing device" as used herein may be any information that allows directly or indirectly determining the processing capacity of the radiographic image for performing the body thickness distribution estimating process. For example, the processing capacity information may be information indicating processing speed of the processing unit and the memory capacity of a computer forming the radiographic image analyzing device, or may be information indicating the type of the imaging apparatus or information indicating the imaging location.

In this case, the processing capacity information may be information indicating the type of the imaging apparatus used to take the subject image.

The "information indicating the type of the imaging apparatus" as used herein may be any information that allows estimating whether or not a processing unit having a sufficient processing performance, such as those used in the imaging chamber of hospitals, is used. For example, the information may indicate a fixed-type radiation source, a portable radiation source, a standard-type console such as those provided in the image interpretation room, a portable console such as a tablet-type terminal, a fixed-type detector panel, or a portable detector panel.

In the radiographic image analyzing device according to the disclosure, the judging unit may execute, based on associating information that associates each imaging location with the first control or the second control, the first control if the imaging location of the subject image is associated with the first control, and may execute the second control if the imaging location of the subject image is associated with the second control.

The "imaging location" as used herein may be any location that allows estimating whether or not the location is an environment where a processing unit having sufficient processing performance is used, such as the imaging chamber of hospitals, or that allows confirming whether or not it is necessary to keep the run time of the body thickness distribution estimating process within an acceptable range. For example, the imaging location may be an imaging chamber, in an ambulance, in a mobile health care clinic, outdoors, in a patient's room, or any other location that is not a medical facility.

In the radiographic image analyzing device according to the disclosure, the judging unit may execute, based on emergency display information that indicates whether or not emergency display of the subject image is necessary, the second control if the emergency display is necessary, and may execute the first control if the emergency display is not necessary.

In the radiographic image analyzing device according to the disclosure, the judging unit may execute, based on associating information that associates each body part shown in the subject image with the first control or the second control, the first control if the body part shown in the subject image is associated with the first control, and may execute the second control if the body part shown in the subject image is associated with the second control.

In the radiographic image analyzing device according to the disclosure, the first termination condition may represent a first threshold value which is an acceptable value of the difference between the estimated image generated by the estimated image generating unit and the subject image, the second termination condition may represent a second threshold value which is an acceptable value of the difference between the estimated image generated by the estimated image generating unit and the subject image, and the second threshold value may be greater than the first threshold value.

In the radiographic image analyzing device according to the disclosure, the second termination condition may represent the upper limit value of the number of iterations of the body thickness distribution modifying process, or the upper limit value of the sum of the run times of the body thickness distribution modifying process.

It is preferred that the radiographic image analyzing device according to the disclosure further comprise: an image processing unit for performing image processing on the subject image using a process parameter depending on the body thickness distribution of the subject to obtain a processed image, and a display control unit for displaying the processed image on a display unit.

According to the disclosure, the first control under which the number of iterations of the iterative control is relatively large and the second control under which the number of iterations of the iterative control is smaller than that under the first control are switched therebetween according to the judgment condition. This allows keeping the run time of the body thickness distribution estimating process within an acceptable range while ensuring high accuracy of the body thickness distribution estimating process.

DETAILED DESCRIPTION OF THE PREFERRED EMBODIMENTS

Figure 1:
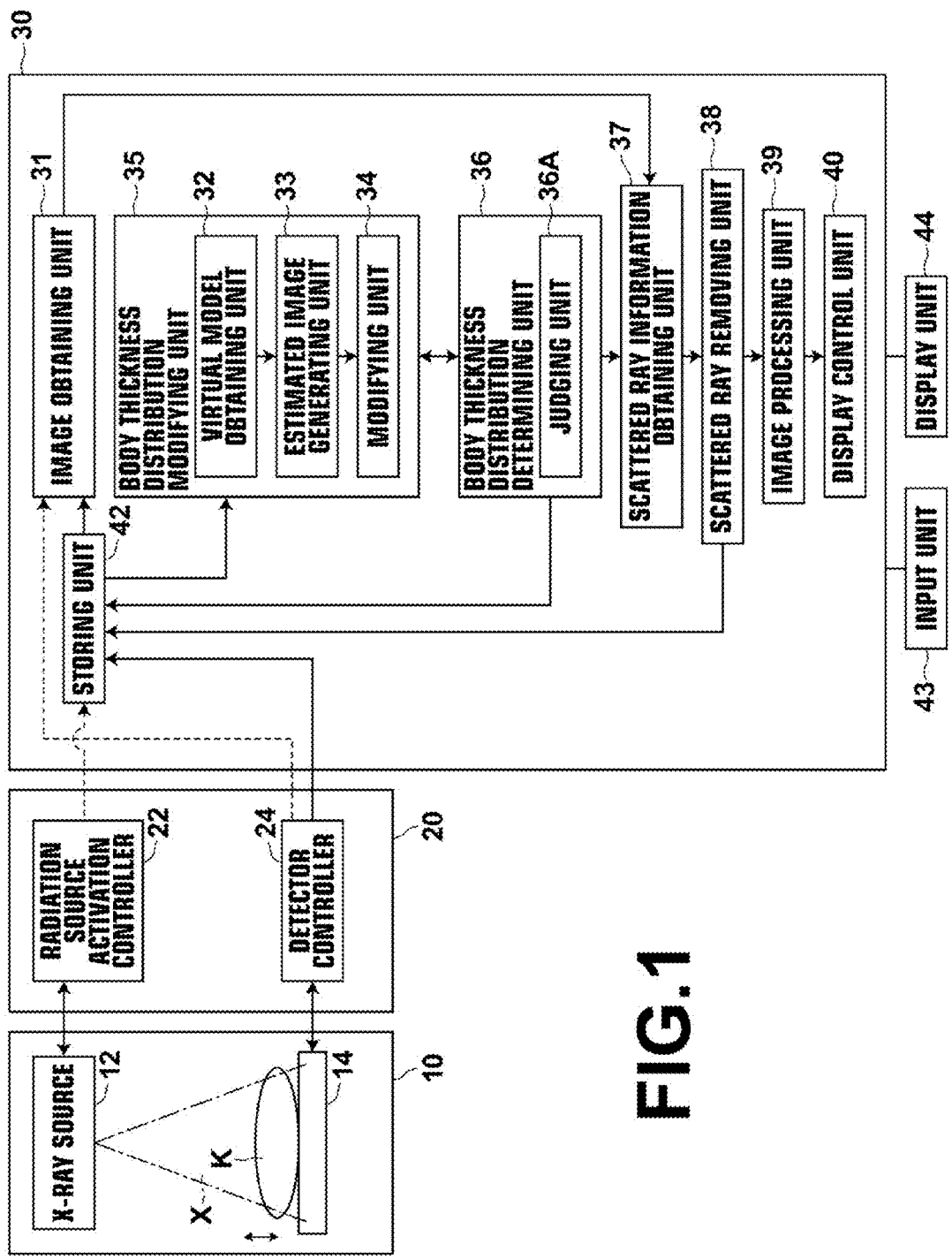
FIG. 1 is a schematic block diagram illustrating the configuration of a radiographic imaging system to which a radiographic image analyzing device according to a first embodiment of the disclosure is applied.

Hereinafter, embodiments of the present disclosure will be described with reference to the drawings. FIG. 1 is a schematic block diagram illustrating the configuration of a radiographic imaging system to which a radiographic image analyzing device according to a first embodiment of the disclosure is applied. As shown in FIG. 1, the radiographic imaging system according to this embodiment includes an imaging unit 10, a control unit 20 for controlling the system, and an image analyzing unit 30 (the radiographic image analyzing device).

The imaging unit 10 includes an x-ray source 12, which applies an x-ray to a subject K, and a radiation detector 14, which detects the x-ray transmitted through the subject K to obtain a radiographic image of the subject K. In this embodiment, no scattered ray removal grid (or grid) for removing scattered rays, which are scattered by the subject K, of the x-ray transmitted through the subject K is disposed between the subject K and the radiation detector 14.

The control unit 20 includes a radiation source activation controller 22, which controls activation of the x-ray source 12 according to a set imaging condition, and a detector controller 24, which controls the radiation detector 14 to obtain a radiographic image (subject image) of the subject and stores the radiographic image (subject image) in a storing unit 42.

The image analyzing unit 30 is a computer including an input unit 43 for receiving various types of input made by the operator to the image analyzing unit 30, the display unit 44, a central processing unit (CPU), a semiconductor memory, a communication interface, and the storing unit 42, such as a hard disk or SSD. A radiographic image analyzing program according to this embodiment is installed on the image analyzing unit 30. When the radiographic image analyzing program is executed, the central processing unit and the memory of the image analyzing unit 30 cooperate to function as an image obtaining unit 31, a body thickness distribution modifying unit 35, a body thickness distribution determining unit 36, a scattered ray information obtaining unit 37, a scattered ray removing unit 38, an image processing unit 39, and a display control unit 40. The input unit 43 is formed by a keyboard, a mouse, a touch panel, etc. The input unit 43 receives various types of input made by the operator to the image analyzing unit 30. The display unit 44 is formed by a CRT, a liquid crystal display, or the like, and displays a radiographic image obtained by the imaging unit 10 and various information necessary for desired operations.

The storing unit 42 stores a subject image Ik that is obtained by an imaging control unit (not shown), which controls the detector controller 24 and the radiation source activation controller 22, and the imaging condition under which the subject image Ik is taken. The storing unit 42 also stores a lookup table LUT, which is generated in advance to associate each density value (pixel value) with a body thickness for each of different imaging conditions. The storing unit 42 also stores a virtual model M of the subject K, the virtual model M having an initial body thickness distribution T0(x,y). The storing unit 42 also stores characteristics information indicating structural objects (in this embodiment, anatomical structural objects, such as the lung fields, bones, and organs) included in the virtual model M for the subject image, locations of the structural objects, characteristics of the structural objects to radiation, etc., which is set in advance based on locations and compositions of the anatomical structural objects, such as the lung fields, bones, etc., in the thoracoabdominal part of a comparative subject. The storing unit 42 also stores various parameters necessary for individual operations, and generated images (such as an estimated primary ray image, an estimated scattered ray image, etc.), as necessary. It should be noted that the "body thickness" as used herein refers to a total thickness of a subject region except an air region present along a traveling path of the applied radiation.

The "imaging condition" as used herein may include at least one of the imaging radiation dose, the tube voltage, the product of the tube current and the exposure time, the distance between the radiation source (ray source) and the detection surface of the radiation detector, the materials of the target and the filter of the radiation source, the type of the radiation detector used for imaging, the amount of air gap (the distance from the subject to the radiation detector), and the presence or absence and the material of a radiation shield, which is provided at the radiation detector, as necessary.

In this embodiment, the imaging radiation dose, the tube voltage, the product of the tube current and the exposure time, and the distance from the radiation source to the detection surface of the radiation detector which are used when the subject image Ik is taken are stored as the imaging condition. It should be noted that the stored imaging condition is used as necessary for operations performed by the body thickness distribution modifying unit 35, operations performed by the scattered ray information obtaining unit 37, and other desired image processing of various types, such as operations performed by the image processing unit 39, which will be described later.

The display control unit 40 displays information necessary for the image analyzing process according to this embodiment, information necessary for imaging control by the control unit 20, etc., on the display unit 44, as necessary.

The image obtaining unit 31 obtains the subject image Ik from the detector controller 24 or the storing unit 42, etc. It should be noted that this embodiment is not intended to limit the present invention, and the invention is applicable to any type of subject. For example, the subject may be any body part of a human body.

The body thickness distribution modifying unit 35 receives a virtual model M having an estimated body thickness distribution $T_n$ inputted by the body thickness distribution determining unit 36, which will be described later, and modifies the estimated body thickness distribution of the virtual model M to output the modified estimated body thickness distribution $T_n$. It should be noted that the number of iterations of a body thickness distribution estimating process performed by the body thickness distribution modifying unit 35 is the n-th time (where n is a natural number). Specifically, the body thickness distribution modifying unit 35 includes: a virtual model obtaining unit 32, which obtains the virtual model having the initial body thickness distribution T0 (the estimated body thickness distribution inputted thereto); an estimated image generating unit 33, which generates, as an estimated image Im, which is an estimate of a radiographic image that would be obtained by radiographic imaging of the subject K, an image by combining an estimated primary ray image Ip, which is an estimate of a primary ray image that would be obtained by radiographic imaging of the obtained virtual model M, and an estimated scattered ray image Is, which is an estimate of a scattered ray image that would be obtained by radiographic imaging of the virtual model M; and a modifying unit 34, which modifies the obtained estimated body thickness distribution $T_n$ such that the difference between the estimated image Im and the subject image Ik is reduced and outputs the modified estimated body thickness distribution $T_n$.

The virtual model obtaining unit 32 obtains the virtual model M of the subject K having the initial body thickness distribution T0. During iteration of the body thickness distribution estimating process, the virtual model M having an estimated body thickness distribution $T_{n-1}$ that is modified at least once by the modifying unit 34, which will be described later, is obtained. The virtual model M is data that virtually represents the subject K with the body thicknesses according to the initial body thickness distribution T0(x,y) being associated with individual positions on the x-y plane. The characteristics information indicating structural objects (in this embodiment, anatomical structural objects, such as the lung fields, bones, and organs) included in the virtual model M, locations of the structural objects, and characteristics of the structural objects to radiation, etc., is set based on locations and compositions of the anatomical structural objects, such as the lung fields, bones, etc., in the thoracoabdominal part of a comparative subject.

In this embodiment, the initial body thickness distribution T0 of the virtual model M of the subject K is generated and obtained by the virtual model obtaining unit 32.

Figure 2:
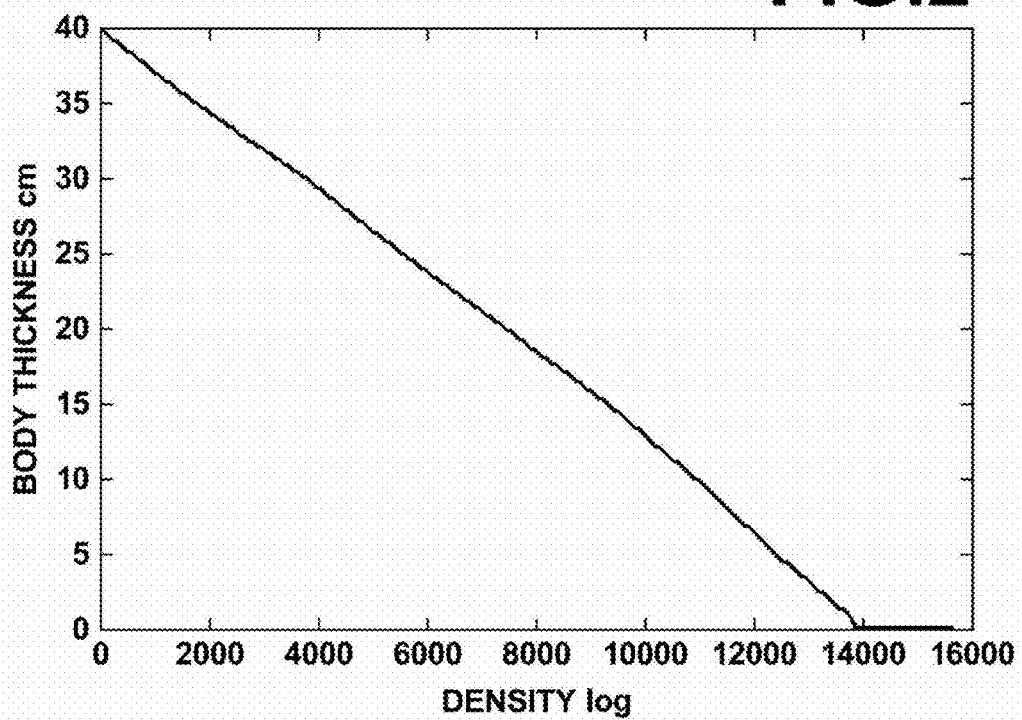
FIG. 2 shows one example of a lookup table of a body thickness distribution.

The virtual model obtaining unit 32 obtains the imaging condition of the subject image Ik, and obtains the lookup table that associates pixel values (density values) with body thicknesses corresponding to the imaging condition of the subject K from the storing unit 42. FIG. 2 shows an example of the lookup table associating pixel values with body thicknesses. Then, the virtual model obtaining unit 32 identifies the body thickness corresponding to the pixel value of each pixel of the subject image Ik based on the table shown in FIG. 2 to obtain the initial body thickness distribution T0 of the subject image Ik. The above-described operation is expressed by the equation (1) below:

$$T_0(x,y) = \mathrm{LUT}(I_k(x,y)) \qquad (1),$$

where Ik(x,y) represents the pixel value of each pixel of the subject image, and T0(x,y) represents the initial body thickness distribution at the pixel position.

It should be noted that, since the initial body thickness distribution of the virtual model M for the subject image is modified by the modifying unit 34, which will be described later, the initial body thickness distribution may represent any distribution, such as the body thickness distribution of a standard human body, or a uniform distribution. The initial body thickness distribution T0 may be generated and obtained when the initial body thickness distribution of each virtual model M is obtained, or may be set in advance before the virtual model M is obtained.

The estimated image generating unit 33 generates, as the estimated image Im of the subject image Ik, which is an estimate of the subject image Ik, an image by combining the estimated primary ray image Ip, which is an estimate of a primary ray image that would be obtained by radiographic imaging of the virtual model M, and the estimated scattered ray image Is, which is an estimate of a scattered ray image that would be obtained by radiographic imaging of the virtual model M, and stores the generated estimated image Im in the storing unit 42.

Figure 3:
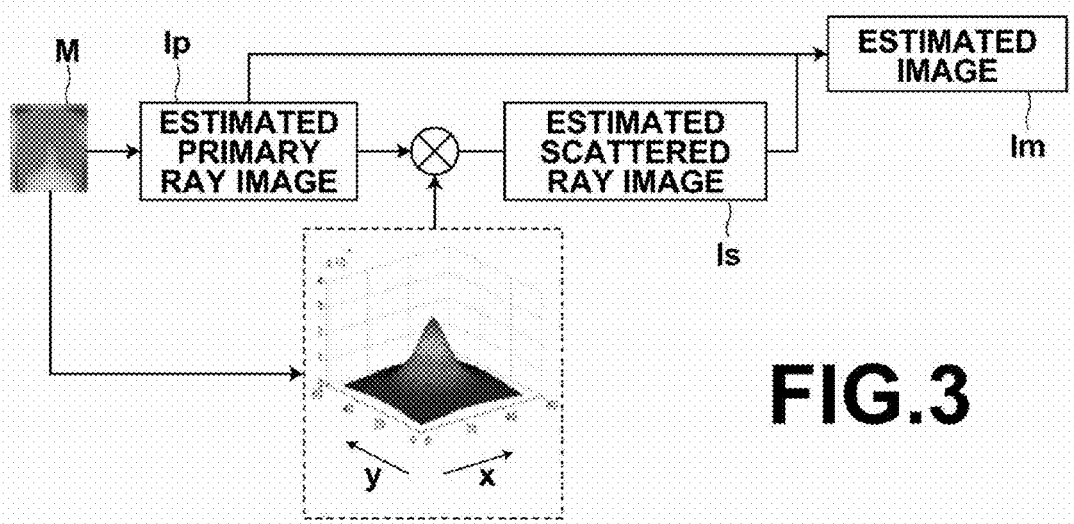
FIG. 3 is a diagram for explaining one example of a method for generating an estimated image.
Figure 4:
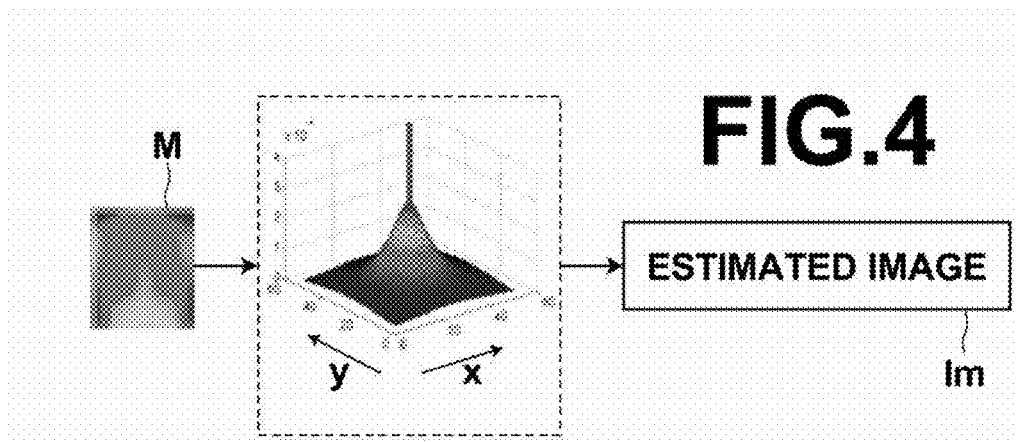
FIG. 4 is a diagram for explaining another example of the method for generating the estimated image.

FIGS. 3 and 4 are diagrams for explaining a method for generating the estimated image Im. As shown in FIG. 3, the estimated image generating unit 33 generates the estimated primary ray image Ip that would be obtained by imaging virtual model M under an imaging condition equivalent to the imaging condition of the subject image Ik according to the equation (2) below, and generates the estimated scattered ray image Is using the generated estimated primary ray image Ip according to the equation (3) below. Then, the estimated image generating unit 33 generates the estimated image Im by combining the estimated primary ray image Ip and the estimated scattered ray image Is, as shown by the equation (4) below. It should be noted that, when the estimated primary ray image Ip and the estimated scattered ray image Is are generated the first time, the initial body thickness distribution T0(x,y) is used in the estimation equations (2) and (3) (n=1 in the equations (2) and (3)).

$$I_p(x, y) = I_o(x, y) \times \exp(-T_{n-1}(x, y) \times \mu), \qquad (2)$$

$$I_s(x, y) = \sum_{x',y'} I_p(x', y') K_s(x, y, T_{n-1}(x', y'), \theta_{x',y'}), \qquad (3)$$

$$I_m(x, y) = I_p(x, y) + I_s(x, y). \qquad (4)$$

In the above equations, (x,y) are coordinates at a pixel position of the subject image Ik, Ip(x,y) is the estimated primary ray image (primary ray pixel value) at the pixel position (x,y), Is(x,y) is the estimated scattered ray image (scattered ray pixel value) at the pixel position (x,y), Io(x,y) is the amount of radiation at the pixel position (x,y), Im(x,y) is the estimated image at the pixel position (x,y), p is a linear attenuation coefficient of the subject, and $K_s(x,y,T_{n-1}(x',y'),\theta_{x',y'})$ is a convolution kernel that represents a point spread function depending on the subject thickness at the pixel position (x,y). It should be noted that the amount of radiation Io(x,y) is an amount of radiation (pixel value) that is detected by the detector when it is assumed that there is no subject, and the amount of radiation Io(x,y) varies depending on the distance (SID) between the radiation source 12 and the detection surface of the radiation detector 14, the tube voltage, and the imaging radiation dose. Further, $\theta_{x',y'}$ represents a parameter specified by the imaging condition and the characteristics information of the virtual model M.

It should be noted that the estimated image Im may be any image which is an estimate of an image that would be obtained by radiographic imaging of the virtual model M and can substantially be regarded as a composite image obtained by adding the estimated primary ray image Ip and the estimated scattered ray image Is. For example, as shown in FIG. 4, in place of the equations (2) to (4), the equation (5) below may be used to generate the estimated image Im by convolution of a kernel that combines the primary ray component and the scattered ray component:

$$I_m(x, y) = \sum_{x',y'} K_{p+s}(x, y, T_{n-1}(x', y'), \theta_{x',y'}). \qquad (5)$$

In the equation (5), $K_{p+s}(x,y,T_{n-1}(x',y'),\theta_{x',y'})$ is a kernel representing a point spread function that combines the primary ray component and the scattered ray component. Further, any model function which allows generation of the estimated image by combining the estimated primary ray image and the estimated scattered ray image of an image obtained by radiographic imaging may be used.

It should be noted that $K_{p+s}(x,y,T_{n-1}(x',y'),\theta_{x',y'})$ can be experimentally found depending on the imaging condition, etc.

In this embodiment, the kernel $K_s(x,y,T_{n-1}(x',y'),\theta_{x',y'})$ or $K_{p+s}(x,y,T_{n-1}(x',y'),\theta_{x',y'})$ is calculated in advance for each imaging condition, and a table that associates each imaging condition with the kernel $K_s(x,y,T_{n-1}(x',y'),\theta_{x',y'})$ or $K_{p+s}(x,y,T_{n-1}(x',y'),\theta_{x',y'})$ is stored in advance in the storing unit 42. Then, the $K_s(x,y,T_{n-1}(x',y'),\theta_{x',y'})$ or $K_{p+s}(x,y,T_{n-1}(x',y'),\theta_{x',y'})$ is found by referencing the table based on irradiation field information, subject information, and the imaging condition during imaging. It should be noted that the kernel $K_s$ or $K_{p+s}$ may be calculated at any timing before the kernel $K_s$ or $K_{p+s}$ is used.

The modifying unit 34 modifies the initial body thickness distribution T0 or the estimated body thickness distribution $T_{n-1}$, which has been modified at least once, of the virtual model M of the subject K based on the subject image Ik and the estimated image Im of the subject image Ik, such that the difference between the subject image Ik and the estimated image Im of the subject image Ik is reduced. Specifically, the modification is performed such that the differences between the pixel values at corresponding positions of the estimated image Im and the subject image Ik are reduced.

To achieve the process of modifying the estimated body thickness distribution $T_{n-1}$, the modifying unit 34 can apply any method that allows obtaining a modified value at each position of the estimated body thickness distribution $T_{n-1}$ such that the difference between the subject image Ik and the estimated image Im is reduced. In this embodiment, the modifying unit 34 calculates, for each partial region formed by one or more pixels of the virtual model M, a body thickness that reduces the difference between the subject image Ik and the estimated image Im with varying the estimated body thickness distribution $T_{n-1}$ of the virtual model M. Then, the modifying unit 34 modifies the body thickness distribution of the virtual model according to the calculated body thickness of each partial region.

In this embodiment, the modifying unit 34 calculates a modified value of the body thicknesses of the estimated body thickness distribution $T_{n-1}$ using a steepest descent method. The modifying unit 34 iteratively calculate $dT_{n-1}(x,y)$, using the equations (6) and (7) below, based on a primary partial differential (gradient) of an error function $f_{error}$, with varying only the body thickness at a certain coordinate position in the $T_{n-1}(x,y)$ among pixels of the virtual model M, to thereby minimize the output value of the error function $f_{error}$. Then, the body thickness at a certain coordinate portion when the output value of the error function $f_{error}$ is minimized is determined as the modified value of the body thickness at the coordinate position. Similarly, the modified value of the body thickness is calculated for each pixel to modify the body thickness distribution at the pixel, and the modified estimated body thickness distribution $T_n$ is obtained and stored in the storing unit 42.

$$T_n(x, y) = T_{n-1}(x, y) - \alpha dt_{n-1}(x, y) \quad (6)$$
$$= T_{n-1}(x, y) - \alpha \frac{d}{dT_{n-1}(x, y)} f_{error},$$

$$\frac{d}{dT_{n-1}(x, y)} f_{error} = \sum_{x',y'} (I_m(x', y') - I_k(x', y')) \quad (7)$$
$$\frac{d}{dT_{n-1}(x, y)} K_{p+s}(x', y', T_{n-1}(x, y), \theta_{x,y}),$$

$$\frac{d}{dT_{n-1}(x, y)} K_{p+s}(x', y', T_{n-1}(x, y)\theta_{x,y}), = \quad (8)$$
$$K_{p+s}(x', y', T_{a-1}(x, y) + dt, \theta_{x,y}) -$$
$$K_{p+s}(x', y', T_{n-1}(x, y), \theta_{x,}).$$

In the equation (6), a is an update factor, which is a parameter representing an update rate of the body thickness. As one example of the method for calculating the differential value portion of $K_{p+s}$ in the equation (7), a change of the value when a very small value dt is added to $T_{n-1}(x,y)$ can be calculated according to the equation (8) above as the value of in the equation (7).

The body thickness distribution determining unit 36 has a function of controlling iteration of the operation performed by the body thickness distribution modifying unit 35. Assuming that the current number of iterations of the operation performed by the body thickness distribution modifying unit 35 is n (where n is a natural number), when n=1, the body thickness distribution determining unit 36 inputs the initial body thickness distribution $T_{n-1}(T0)$ to the body thickness distribution modifying unit 35, causes the virtual model obtaining unit 32 to obtain the virtual model M having the estimated body thickness distribution $T_{n-1}(T0)$, causes the estimated image generating unit 33 to generate an estimated image Im from the virtual model M, causes the modifying unit 34 to modify the initial body thickness distribution T0, updates the value of n by incrementing the value by one (i.e., n=n+1), and causes the modified initial body thickness distribution to be outputted as the estimated body thickness distribution $T_n(T1)$. Subsequently, the body thickness distribution determining unit 36 controls iterative execution of the body thickness distribution modifying process (the series of operations shown in steps S06, S02, and S03, which will be described later), where the body thickness distribution determining unit 36 causes the modifying unit 34 to modify the estimated body thickness distribution $T_{n-1}$ of the virtual model M to output the estimated body thickness distribution $T_n$, and inputs the virtual model M having the outputted estimated body thickness distribution $T_n$ to the virtual model obtaining unit 32 so that the virtual model obtaining unit 32 obtains the virtual model M, and causes the estimated image generating unit 33 to generate the estimated image Im from the virtual model M.

Further, the body thickness distribution determining unit 36 determines whether or not the body thickness distribution modifying process satisfies a termination condition. If it is determined that the termination condition is not satisfied, the body thickness distribution determining unit 36 executes the body thickness distribution modifying process. If it is determined that the termination condition is satisfied, the body thickness distribution determining unit 36 determines the estimated body thickness distribution that is outputted by the body thickness distribution modifying process when the termination condition is satisfied to be used as the body thickness distribution of the subject. For example, if the number of iterations of the body thickness distribution modifying process when the termination condition is first satisfied is n, the estimated body thickness distribution $T_n$ is determined to be used as the body thickness distribution Tk of the subject. Then, the body thickness distribution determining unit 36 stores the body thickness distribution Tk of the subject in the storing unit 42.

The body thickness distribution determining unit 36 has a first termination condition and a second termination condition, which is different from the first termination condition, as the termination condition, and includes a judging unit 36A which switches, according to a judgment condition, between a first control under which the body thickness distribution modifying process is iteratively executed until the first termination condition is satisfied, and a second control under which the body thickness distribution modifying process is iteratively executed until the second termination condition is satisfied.

In recent years, there is an increasing demand from the medical sites for a high quality processed image of the subject image which is suitable for observation to be displayed for diagnostic imaging of the patient, etc. Further, in order to display the processed image generated from the subject image for diagnostic imaging, a certain time is required for obtaining the subject image Ik of the subject K, performing the series of operations to estimate the body thickness distribution of the subject image Ik, and performing desired image processing, such as scattered ray removal, gradation processing, noise suppression, dynamic range adjustment, frequency emphasis, etc., using the determined body thickness distribution of the subject image Ik to generate the processed image. However, there is also a strong demand from the medical sites for reducing the time taken to obtain the subject image and display the processed image. It is therefore preferred to keep the time taken for displaying the processed image within an acceptable range while ensuring high quality of the processed image.

The disclosure is directed to control the time taken for the body thickness distribution estimating process performed in the process of determining the body thickness distribution to keep the run time of the body thickness distribution estimating process within an acceptable range while ensuring high accuracy of the body thickness distribution estimating process. For this purpose, the judging unit 36A switches, based on a judgment condition, between the first control under which the number of iterations of the loop process (body thickness distribution modifying process) included in the body thickness distribution estimating process is relatively large, and the second control under which the number of iterations of the loop process is relatively small so that one of the first control and the second control is executed. This allows controlling the run time of the body thickness distribution estimating process (the process to determine the body thickness distribution) in the time required for obtaining a subject image and display the processed image. It should be noted that, for the second control, the second termination condition is set such that the time taken for iterations of the body thickness distribution modifying process is within the acceptable range. For the first control, the first termination condition is set with respect to any other matter, such as high accuracy of the body thickness distribution. In any case, the first termination condition and the second termination condition are set such that the number of iterations of the body thickness distribution modifying process under the second control is smaller than the number of iterations of the body thickness distribution modifying process under the first control. In this embodiment, the body thickness distribution estimating process is performed by the body thickness distribution modifying unit and the body thickness distribution determining unit (for example, the operations shown in steps S02 to S07 in FIG. 6, which will be described later).

As the judgment condition, any condition that allows determining whether or not it is necessary to limit the time taken for iterations of the body thickness distribution modifying process within an acceptable range may be set.

In this embodiment, the judging unit 36A estimates an estimated run time, which is an estimate of a sum of the run times of the body thickness distribution modifying process that is iteratively executed until the first termination condition is satisfied, based on time-series transition of the difference between the estimated image Im and the subject image Ik during the iterations of the body thickness distribution modifying process. Then, the second control is executed if the estimated run time is greater than a first time limit, and the first control is executed if the estimated run time is not greater than the first time limit. Now, this example is described with reference to FIG. 5. It should be noted that the judging unit 36A may determine whether or not the sum of measurements of the run times of the body thickness distribution modifying process is greater than the first time limit, or may estimate the sum of the run times of the body thickness distribution estimating process to indirectly determine whether or not the sum of the run times of the body thickness distribution modifying process is greater than the first time limit.

Figure 5:
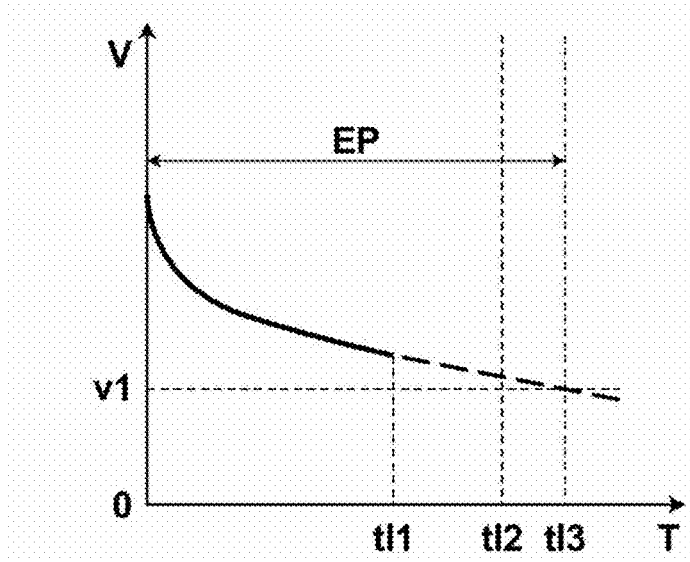
FIG. 5 is a diagram for explaining an example of a judgment condition.

FIG. 5 shows accumulated values of the run times of the body thickness distribution modifying process along the horizontal axis, and difference values between the subject image and the estimated image along the vertical axis. The first termination condition represents an acceptable value v1 of the difference between the subject image and the estimated image. In FIG. 5, the solid line shows time-series transition of the already calculated difference between the estimated image Im and the subject image Ik, and the dashed line shows time-series transition of the estimated difference between the estimated image Im and the subject image Ik. As shown in FIG. 5, as the body thickness distribution determining unit 36 iteratively executes the body thickness distribution modifying process until the first termination condition is satisfied, the difference between the subject image Ik and the estimated image Im is gradually reduced.

In this example, the judgment condition represents a first time limit t12 that is set by the user based on an acceptable waiting time. The judging unit 36A calculates an approximate curve of time-series data of the difference between the estimated image Im and the subject image Ik from the start of the first iteration of the body thickness distribution modifying process, finds a line tangent to the approximate curve at a certain reference time t11 (see the dashed line in FIG. 5), and calculates a time t13 at which the tangent line reaches the acceptable value v1, to thereby estimate an estimated run time EP, which is an estimate of a sum of the run times of the iteratively executed body thickness distribution modifying process from the start of the first iteration of the body thickness distribution modifying process until the first termination condition is satisfied. Then, if the estimated run time is greater than the first time limit t12, the second control is executed. On the other hand, if the sum of the run times of the iteratively executed body thickness distribution modifying process is not greater than the first time limit, the first control is executed.

In the above-described example, the total run time of the iteratively executed estimated body thickness modifying process can be kept within an acceptable range by the relatively simple method, i.e., by determining whether or not the sum of the run times of the iteratively executed body thickness distribution modifying process is greater than the first time limit.

Alternatively, based on processing capacity information which indicates the processing capacity of the radiographic image analyzing device, for example, the judging unit 36A may execute the second control if the processing capacity is lower than a certain processing level, and may execute the first control if the processing capacity is not lower than the certain processing level.

The higher the processing capacity of the radiographic image analyzing device, the faster the execution speed of the body thickness distribution modifying process. Therefore the certain processing level of the processing capacity is set such that the run time under the first control is within an acceptable range based on the processing capacity of the radiographic image analyzing device. For example, the processing capacity may be classified into different levels depending on specifications of the central processing unit and memory size of the computer forming each radiographic image analyzing device. In this case, depending on the processing capacity of the radiographic image analyzing device, if the processing capacity is lower than the certain processing level, the second control can be executed to keep the total run time of the iteratively executed estimated body thickness modifying process within an acceptable range.

In the above-described example, the processing capacity information may be any information that indicates the processing capacity of the image processing unit. For example, the processing capacity information that indicates the processing capacity of the image processing unit may be information indicating the type of the imaging apparatus used to take the subject image.

It should be noted that the "information indicating the type of the imaging apparatus" as used herein may be any information that allows estimating whether or not a processing unit that has sufficient processing performance, such as those used in the imaging chamber of hospitals, is used. For example, the information may indicate a fixed-type radiation source, a portable radiation source, a standard-type console such as those provided in the image interpretation room, a portable console such as a tablet-type terminal, a fixed-type detector panel, or a portable detector panel. A portable imaging apparatus (such as a portable radiation source, a portable detector panel, or a portable console) has a limited processing capacity to meet demands for weight reduction and size reduction. Therefore the judgment condition may be set such that the second control is executed if the imaging apparatus information indicates a portable imaging apparatus. On the other hand, a fixed-type apparatus (such as a fixed-type radiation source, a fixed-type detector panel, or a standard-type console used in an image interpretation room) that is provided in the imaging chamber of hospitals is assumed to have at least a certain level of processing capacity, and the judgment condition may be set such that the first control is executed if the imaging apparatus information indicates a fixed-type imaging apparatus.

Still alternatively, based on associating information that associates each imaging location with the first control or the second control, for example, the judging unit 36A may execute the first control if the imaging location of the subject image is associated with the first control, and may execute the second control if the imaging location of the subject image is associated with the second control.

The "imaging location" as used herein may be any location that allows estimating whether or not the location is an environment where a processing unit having sufficient processing performance, such as those used in the imaging chamber of hospitals, is used, or that allows confirming whether or not it is necessary to keep the run time of the body thickness distribution estimating process within an acceptable range. For example, the type of the imaging location may include an imaging chamber, in an ambulance, in a mobile health care clinic, outdoors, in a patient's room, or any other location that is not a medical facility. The associating information may be set such that the first control is executed if the imaging location indicates an environment where a processing unit having a sufficient processing performance, such as those used in the imaging chamber of hospitals, is used, and the second control is executed if the imaging location indicates an environment where a processing unit having a sufficient processing performance, such as those used in the imaging chamber of hospitals, is not used (such as in an ambulance, in an ambulance emergency response vehicle, in a mobile health care clinic, outdoors, in a patient's room, or any other location that is not a medical facility). Alternatively, the associating information may be set such that the second control is executed if the imaging location indicates a location that allows confirming that it is necessary to keep the run time of the body thickness distribution estimating process within an acceptable range (such as in an ambulance, in an ambulance emergency response vehicle, in a mobile health care clinic, outdoors, in a patient's room, or any other location that is not a medical facility), and the first control is executed if the imaging location indicates a location that allows confirming that it is not necessary to keep the body thickness distribution estimating process within the acceptable range.

In a case where radiographic imaging is performed at a location other than an imaging chamber, it is impossible to take a sufficient measure to suppress scattered rays entering the radiation detector from the imaging environment, and there is a demand for a displaying the processed image as soon as possible after the radiographic imaging to allow checking the influence of the scattered rays on the processed image and determining whether or not it is necessary to retake the image. In the case where the judging unit 36A switches between the first control and the second control depending on the imaging location, the above-described demand can be preferably met by setting the associating information to associate an imaging location where no measure against the scattered rays is taken with the second control.

Based on emergency display information that indicates whether or not it is necessary to perform emergency display of the subject image, the judging unit 36A executes the second control if emergency display is necessary, and executes the first control if it is not necessary to perform emergency display.

There is a demand for displaying the processed image, which is obtained by applying necessary image processing to the subject image taken, as soon as possible after the subject image is taken when the emergency level is high, such as during diagnostic imaging of an emergency patient. If it is necessary to perform the emergency display, it is effective to display the processed image as soon as possible for image observation by executing the second control. This allows providing information that is useful for the emergency medical care faster. For example, the displayed processed image can be used to determine the hospital where an appropriate doctor for the subject being conveyed by the emergency vehicle is present, or the processed image can be quickly sent to the hospital before the emergency vehicle arrives at the hospital.

The information used to determine whether or not it is necessary to perform the emergency display of the subject image may be obtained by any method. For example, the determination may be made such that it is necessary to perform the emergency display when input of an instruction to perfume the emergency display by the user is received, and it is not necessary to perform the emergency display when no input of an instruction to perfume the emergency display by the user is received.

For a body part for which high image quality is not required or a body part with small thickness variation in the body thickness distribution, for example, the judging unit 36A may execute the second control, and the judging unit 36A may execute the first control for the other body parts. For example, based on associating information that associates each body part of the subject with the first control or the second control, the judging unit 36A may execute the first control for a body part of the subject with which the first control is associated, and may execute the second control for a body part of the subject with which the second control is associated. Information as to the body part of the subject image may be obtained by any method. For example, the body part of the subject image may be obtained from order information (information of the instruction to perform imaging), or may be obtained from known image recognition information.

In this case, if the operation to generate a processed image from a subject image is successively performed, efficiency of generation of the processed images from the subject images can be improved by appropriately switching between the first control and the second control depending on the body part, without requiring input by the user.

Alternatively, based on information indicating whether the subject image is a moving image or a still image, the judging unit 36A may execute the first control if the subject image is a still image, and may execute the second control if the subject image is a moving image. This is to meet a demand with respect to a moving image for displaying the processed image, which is generated by applying necessary image processing to the subject image, as soon as possible to prevent time delay. Further, after the body thickness distribution is determined for a frame image forming the moving image, it is preferred to use the determined body thickness distribution for the other frame images forming the same moving image. This allows suppressing time delay and reducing computational load when compared to a case where the body thickness distribution is determined for each frame image.

It is preferred to select an appropriate termination condition in a timely manner depending on the matters required as the first termination condition and the second termination condition.

In this embodiment, the first termination condition represents a first threshold value, which is an acceptable value of the difference between the estimated image generated by the estimated image generating unit and the subject image. The second termination condition represents a second threshold value, which is an acceptable value of the difference between the estimated image generated by the estimated image generating unit and the subject image, and the second threshold value is greater than the first threshold value. In this case, the run time under the second control can be reduced relative to the run time under the first control by the simple method. This also facilitates controlling the ratio of the run time under the second control relative to the run time under the first control.

The first termination condition and the second termination condition are described in more detail. Each of the first termination condition and the second termination condition represents a threshold value for an error value $V_{error}$ which represents the difference between the subject image Ik and the estimated image Im (the first threshold value, which is an acceptable value for the difference between the subject image Ik and the estimated image Im). A threshold value (the second threshold value) for the error value $V_{error}$ under the second condition is set greater than the threshold value (the first threshold value) for the error value $V_{error}$ under the first condition. As the first threshold value, an appropriate value for the target accuracy is set in advance. As the second threshold value, an appropriate value for the acceptable run time is set in advance.

Now, how the body thickness distribution determining unit 36 makes a determination as to the first termination condition is described. The body thickness distribution determining unit 36 defines the error value $V_{error}$ representing the difference between the subject image Ik and the estimated image Im as shown by the equations (9) and (10) below, and determines whether or not the error value $V_{error}$ is not greater than the threshold value as the termination condition. Further, as shown by the equation (10) below, the body thickness distribution determining unit 36 defines an error function $f_{error}$ as a squared sum of pixel values of a difference image Id, which is generated by subtracting the estimated image Im from the subject image Ik. It should be noted that, to the first termination condition, any determination technique that allows determining when the difference between the subject image Ik and the estimated image Im becomes sufficiently small and acceptable is applicable.

$$V_{error} = f_{error}(I_m(x, y), I_k(x, y)), \quad (9)$$

$$f_{error}(I_m(x, y), I_k(x, y)) = \sum_{x,y} (I_m(x, y) - I_k(x, y))^2. \quad (10)$$

The above-described example is not intended to limit the invention, and the error function $f_{error}$ can be defined in any manner that can express the difference between the subject image Ik and the estimated image Im. For example, as shown by the equation (11) below, the error function $f_{error}$ may be defined as a sum of absolute values of pixel values of the difference image Id, which is generated by subtracting the estimated image Im from the subject image Ik:

$$f_{error}(I_m(x, y), I_k(x, y)) = \sum_{x,y} |I_m(x, y) - I_k(x, y)|. \quad (11)$$

It should be noted that the identical elements in the equations (1) to (11) are denoted by the same symbols, and the descriptions thereof are not repeated. Any optimization technique for minimizing the error value $V_{error}$ representing the difference between the estimated image Im and the subject image Ik is applicable, and examples thereof include a simplex method, a steepest descent method, and a conjugate gradient method.

The second termination condition may represent, for example, the upper limit value of the number of iterations of the body thickness distribution modifying process. For example, the limit value of the number of iterations of the body thickness distribution modifying process may be set by executing the first control using a plurality of subject image samples, and setting a value which is sufficiently smaller than the average value, or the like, of the resulting number of iterations of the process using the samples as the limit value. This allows keeping the run time of the iteratively executed estimated body thickness modifying process within an acceptable range by the simple method.

Figure 7:
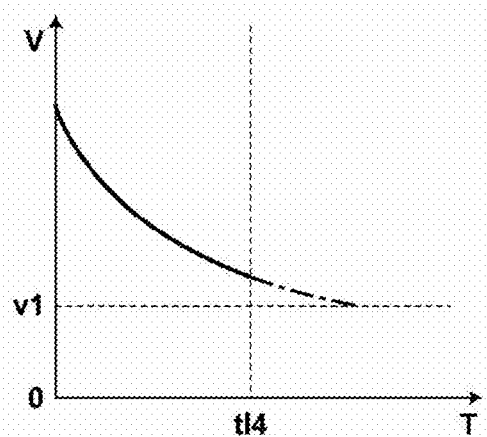
FIG. 7 is a diagram for explaining an example of a termination condition.

Alternatively, for example, the second termination condition may represent the upper limit value of the sum of the run times of the iteratively executed body thickness distribution modifying process. FIG. 7 is a diagram for explaining the example of the second termination condition, where accumulated values of the run times of the body thickness distribution estimating process are shown along the horizontal axis, and difference values between the subject image and the estimated image are shown along the vertical axis. As shown in FIG. 7, as the body thickness distribution determining unit 36 iteratively executes the body thickness distribution modifying process, the difference between the subject image Ik and the estimated image Im is gradually reduced. The first termination condition represents an acceptable value v1 of the difference between the subject image and the estimated image, and the second termination condition represents an upper limit value t14 of the sum of the run times of the body thickness distribution modifying process. In the case where the second control is executed, the body thickness distribution determining unit 36 iteratively executes the body thickness distribution modifying process, and when the sum of the run times of the body thickness distribution modifying process exceeds the upper limit value t14, the body thickness distribution modifying process is not executed any more, and the estimated body thickness distribution that is modified by the last execution of the body thickness distribution modifying process is determined to be used as the body thickness distribution Tk of the subject K (see the solid line in FIG. 7). On the other hand, in the case where the first control is executed, the body thickness distribution determining unit 36 iteratively executes the body thickness distribution modifying process until the acceptable value v1 is satisfied, and determines the estimated body thickness distribution that is modified by the last execution of the body thickness distribution modifying process to be used as the body thickness distribution Tk of the subject K (see the dashed-dotted line in FIG. 7).

It is not preferred that the run time exceed the acceptable range before the difference between the subject image Ik and the estimated image Im converges to satisfy the first termination condition. By setting the second termination condition to represent the upper limit value t14 of the sum of the run times of the body thickness distribution modifying process, the total run time of the iteratively executed estimated body thickness modifying process can be kept within an acceptable range by the simple and reliable method. Further, by switching between the first termination condition which is set such that desired accuracy is satisfied and the second termination condition which is set such that a desired acceptable time is satisfied, the demands for accuracy of the body thickness distribution estimating process as high as possible and limitation on the run time of the body thickness distribution estimating process can be preferably met. It should be noted that the judging unit 36A may determine whether or not the sum of the run times of the body thickness distribution modifying process is greater than the upper limit value, or may indirectly determine whether or not the sum of the run times of the body thickness distribution modifying process is greater than the upper limit value by determining whether or not the sum of the run times of the body thickness distribution estimating process is greater than the upper limit value. Further, the second termination condition may represent any condition that allows making the sum of the run times of the body thickness distribution modifying process or the number of iterations of the body thickness distribution modifying process relatively smaller than that under the first termination condition.

The scattered ray information obtaining unit 37 uses the obtained body thickness distribution Tk to obtain the estimated primary ray image of the subject image Ik according to the equation (2) and obtain the estimated scattered ray image Is(x,y) of the subject image Ik(x,y) according to the equation (3).

The scattered ray removing unit 38 subtracts the estimated scattered ray image Is(x,y) of the subject image Ik from the subject image Ik(x,y) to generate the scattered ray-removed image from which influence of the scattered rays is removed, and stores the scattered ray-removed image in the storing unit 42.

The image processing unit 39 performs necessary image processing, such as noise removal processing for removing noise, gradation processing, and frequency processing, on the subject image Ik to obtain a processed radiographic image. The image processing unit 39 stores the processed image having been subjected to the necessary image processing in the storing unit 42. The image processing unit 39 may perform the necessary image processing on the subject image Ik in any manner, such as performing the necessary image processing directly on the subject image Ik, or performing the necessary image processing on the subject image Ik having been subjected to the scattered ray removal (i.e., the scattered ray-removed image).

Figure 6:
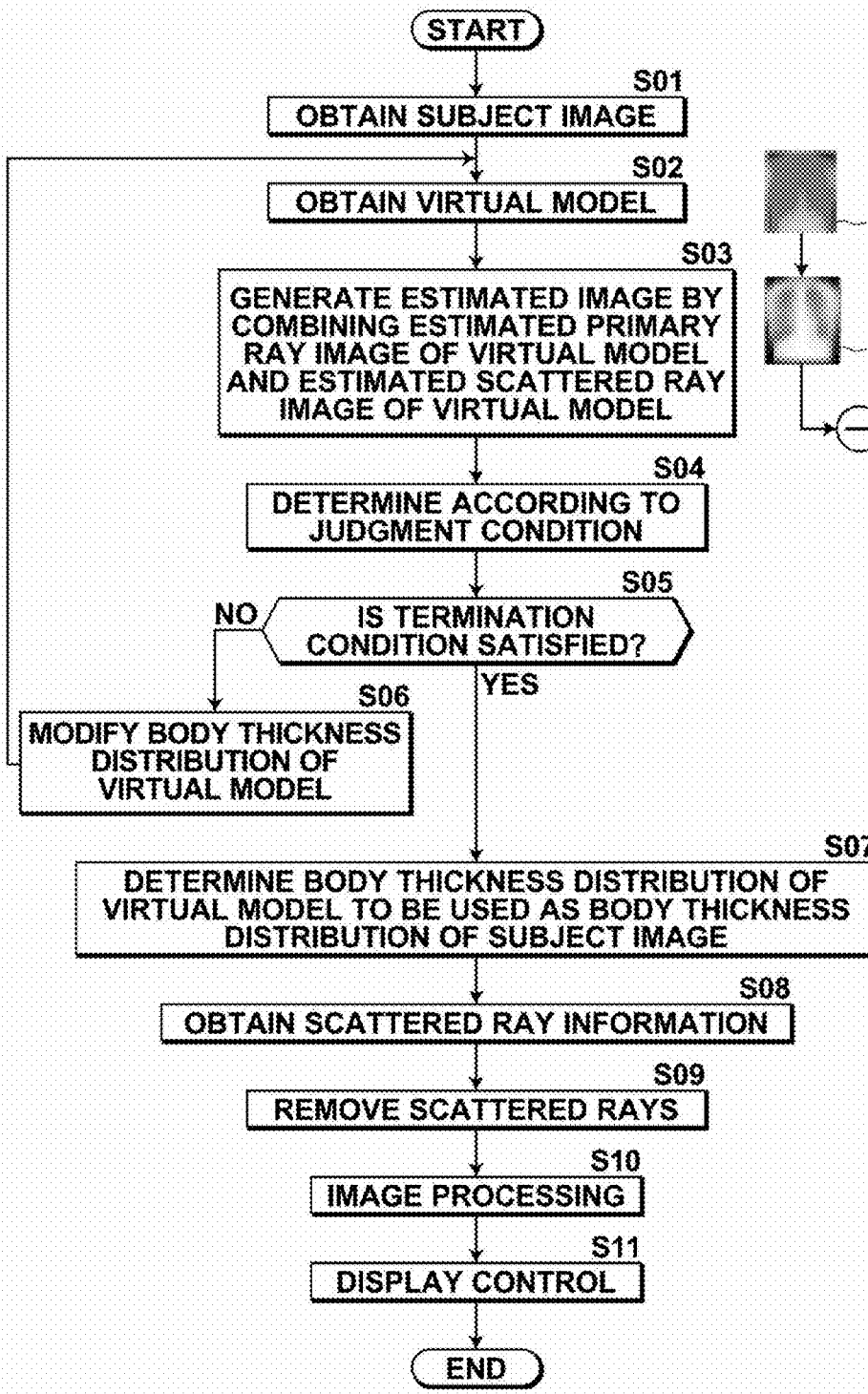
FIG. 6 is a flow chart illustrating a process performed by the radiographic image analyzing device according to the embodiment.

Now, with reference to the flow chart shown in FIG. 6, the flow of a radiographic image analyzing process performed by the image analyzing unit 30 according to this embodiment is described.

First, the image obtaining unit 31 obtains the subject image Ik, which is obtained by radiographic imaging of the patient which is the subject K, from the storing unit 42 (S01).

Then, the virtual model obtaining unit 32 obtains the virtual model M of the subject K having the initial body thickness distribution T0(x,y) from the storing unit 42 (S02).

Then, the estimated image generating unit 33 generates the estimated image Im by combining the estimated primary ray image Ip, which is an estimate of an image that would be obtained by imaging the virtual model M under an imaging condition equivalent to the imaging condition of the subject image, and the estimated scattered ray image Is, which is an estimate of an image that would be obtained by imaging the virtual model M under the imaging condition equivalent to the imaging condition of the subject image (S03).

Subsequently, the judging unit 36A determines whether to execute the first control or the second control according to the judgment condition that is set in advance (S04).

If the first control is executed, the body thickness distribution determining unit 36 uses the first termination condition as the termination condition. If the second control is executed, the body thickness distribution determining unit 36 uses the second termination condition as the termination condition. If the termination condition is not satisfied (S05, No), the body thickness distribution determining unit 36 causes the modifying unit 34 to modify the estimated body thickness distribution $T_{n-1}$ (or the initial body thickness distribution T0 when n=1), update the value of n by incrementing the value by one (i.e., n=n+1), and perform the modifying process to output the modified body thickness distribution as the estimated body thickness distribution $T_n$ (S06).

When the modified estimated body thickness distribution $T_n$ is outputted, the body thickness distribution determining unit 36 causes the virtual model obtaining unit 32 to obtain the modified estimated body thickness distribution $T_n$ (S02). Then, for the obtained estimated body thickness distribution $T_n$, the body thickness distribution determining unit 36 causes the estimated image generating unit 33 to generate the estimated image Im by combining the estimated primary ray image Ip, which is an estimate of an image that would be obtained by imaging the virtual model M having the estimated body thickness distribution $T_n$ under the imaging condition equivalent to the imaging condition of the subject image, and the estimated scattered ray image Is, which is an estimate of an image that would be obtained by imaging the virtual model M under the imaging condition equivalent to the imaging condition of the subject image (S03). Then, the body thickness distribution determining unit 36 determines whether to execute the first control or the second control according to the judgment condition (S04).

Thereafter, the operation (S06) in which the modifying unit 34 modifies the estimated body thickness distribution $T_{n-1}$, updates the value of n by incrementing the value by one (i.e., n=n+1), and outputs the modified body thickness distribution as the estimated body thickness distribution $T_n$, the operation (S02) in which the virtual model obtaining unit 32 obtains the modified estimated body thickness distribution $T_n$, the operation (S03) in which the estimated image generating unit 33 generates an estimated image Im of the virtual model M having the estimated body thickness distribution $T_n$, the operation (S04) in which the judging unit 36A makes determination according to the judgment condition, and the operation (S05) in which the body thickness distribution determining unit 36 determines whether or not the termination condition (the first termination condition under the first control, or the second termination condition under the second control) is satisfied are iterated in this order until the termination condition is satisfied. It should be noted that the operations in steps S06, S02, and S03 correspond to the estimated body thickness modifying process of this embodiment, and the operations in steps S02-S07 correspond to the body thickness distribution estimating process of this embodiment.

If it is determined that the termination condition is satisfied (S05, Yes), the body thickness distribution determining unit 36 determines the modified estimated body thickness distribution $T_n$ that is modified when the termination condition is satisfied to be used as the body thickness distribution Tk of the subject image Ik (S07).

Then, the scattered ray information obtaining unit 37 uses the obtained body thickness distribution Tk to obtain the estimated primary ray image of the subject image Ik according to the equation (2), and obtains the estimated scattered ray image Is(x,y) of the subject image Ik(x,y) according to the equation (3) (S08). Then, the scattered ray removing unit 38 subtracts the estimated scattered ray image Is(x,y) of the subject image Ik from the subject image Ik(x,y) to generate the scattered ray-removed image from which influence of scattered rays is removed, and stores the scattered ray-removed image in the storing unit 42 (S09).

Subsequently, the image processing unit 39 performs necessary image processing on the scattered ray-removed image using process parameters depending on the determined body thickness distribution Tk of the subject to obtain the processed image (S10). Then, the display control unit 40 exerts display control to display the processed image on the display unit 44 until input of an instruction to end the display by the user is received (S11).

According to the embodiments of the disclosure, the estimated image Im is generated by combining the estimated primary ray image Ip and the estimated scattered ray image Is, each of which is an estimate of an image that would be obtained by radiographic imaging of the virtual model M, and the body thickness distribution of the virtual model M is modified such that the difference between the estimated image Im and the subject image Ik is reduced. This allows accurately modifying the estimated body thickness distribution $T_n$ such that the estimated image Im approximates the subject image Ik based on the difference between the subject image Ik and the estimated image Im, and accurately determining the body thickness distribution Tk of the subject image Ik by determining the modified estimated body thickness distribution $T_n$ of the virtual model M to be used as the body thickness distribution Tk of the subject K. With the conventional methods, it is difficult to calculate an accurate body thickness distribution since a radiographic image that is taken without using a grid includes significant influence of a scattered ray component. Whereas, according to the technique of the embodiments of the disclosure, the estimated body thickness distribution $T_n$ is accurately modified such that the estimated image Im approximates the subject image Ik, and the modified estimated body thickness distribution $T_n$ is determined to be used as the body thickness distribution Tk of the subject K. This allows obtaining the body thickness distribution Tk with higher accuracy than those obtained by the conventional methods when the subject image Ik is taken without using a grid.

Further, as shown in the embodiments of the disclosure, the virtual model obtaining unit 32 further obtains the virtual model M having the modified estimated body thickness distribution $T_n$, the estimated image generating unit 33 further generates the estimated image Im from the virtual model M having the modified estimated body thickness distribution $T_n$, and the modifying unit 34 further modifies the estimated body thickness distribution $T_n$ of the virtual model M such that the difference between the generated estimated image Im and the subject image Ik is reduced. This allows more accurately modifying the body thickness distribution T such that the estimated image Im more closely approximates the subject image Ik by iterating the modification of the body thickness distribution T based on the virtual model having the modified estimated body thickness distribution $T_n$, and more accurately determining the body thickness distribution Tk of the subject image Ik by determining the modified estimated body thickness distribution $T_{n+1}$ of the virtual model M to be used as the body thickness distribution Tk of the subject K.

Further, the body thickness distribution determining unit 36 includes the judging unit 36A, and the judging unit 36A switches, based on the judgment condition, between the first control under which the number of iterations of the loop process (the body thickness distribution modifying process) is relatively large and the second control under which the number of iterations of the loop process is relatively small so that one of the first control and the second control is executed. This allows controlling the run time of the iteratively executed body thickness distribution estimating process included in the time required for obtaining the subject image and display the processed image. When the judging unit 36A executes the second control, the body thickness distribution is calculated with accuracy according to the second termination condition, while keeping the time taken for the body thickness distribution modifying process within an acceptable range. When the judging unit 36A executes the first control, the body thickness distribution is calculated with high accuracy according to the first termination condition. By switching between the first control and the second control to execute the control in this manner, the run time of the body thickness distribution estimating process can be kept within an acceptable range while ensuring high accuracy of the body thickness distribution estimating process. As a result, the time required to obtain the subject image and display the processed image can be kept within the acceptable time, and this helps to improve efficiency of image observation by the user.

Further, as shown in the embodiments of the disclosure, the body thickness distribution determining unit 36 determines the estimated body thickness distribution $T_n$ of the virtual model M to be used as the body thickness distribution Tk of the subject K when the difference between the subject image Ik and the estimated image Im becomes sufficiently small and acceptable. This allows iteratively modifying the body thickness distribution such that the body thickness distribution of the estimated image Im approximates the body thickness distribution of the subject image Ik, to thereby determine a very accurate body thickness distribution of the subject image. Further, the body thickness distribution determining unit 36 determines whether or not the difference between the subject image Ik and the estimated image Im is not greater than the threshold value. This allows preferably determining whether or not the difference between the subject image Ik and the estimated image Im is sufficiently small and acceptable to iteratively modify the body thickness distribution such that the body thickness distribution of the estimated image Im approximates the body thickness distribution of the subject image Ik, to thereby very accurately determine the body thickness distribution of the subject image.

Further, in the embodiments of the disclosure, the modifying unit 34 modifies the body thickness distribution of the virtual model such that the sum of absolute values of pixel values of the difference image between the estimated image and the subject image or the squared sum of pixel values of the difference image is reduced. This allows preferably determining the magnitude of the difference between the subject image Ik and the estimated image Im.

Further, as shown in the embodiments of the disclosure, the modifying unit 34 calculates, for each partial region formed by one or more pixels of the virtual model M, the body thickness of the partial region that minimizes the difference between the subject image Ik and the estimated image Im by varying the body thickness of the partial region in the estimated body thickness distribution $T_{n-1}$ of the virtual model M, and modifies the body thickness distribution of the virtual model M according to the calculated body thickness of each partial region. This allows accurately calculating the modified value of the body thickness at each pixel to obtain the preferably modified estimated body thickness distribution $T_n$.

According to the embodiments of the disclosure, the scattered ray information obtaining unit 37 which obtains scattered ray information about estimated scattered rays in the subject image using the determined body thickness distribution Tk of the subject K, and the scattered ray removing unit 38 which removes scattered rays in the subject image based on the obtained scattered ray information are provided. This allows obtaining a processed image having been subjected to accurate scattered ray removal. Any method can be used to obtain the scattered ray information, and any method can be used to remove the scattered rays based on the scattered ray information.

The estimated image generating unit 33 may obtain characteristics information indicating structural objects included in the subject image Ik, locations of the structural objects, and characteristics of the structural objects to radiation as characteristics information of the virtual model M, and may generate the estimated image Im by selecting a parameter used to calculate the estimated image Im depending on the structural object corresponding to each position of the virtual model M based on the characteristics information. For example, based on the characteristics information, the linear attenuation coefficient in the equation (2), which is used to generate the estimated primary ray image Ip from the virtual model M according to the equation (2), may be changed depending on the structural object (the composition of the structural object) at each position. In an image obtained by radiographic imaging, the primary ray component and the scattered ray component vary in a complicated manner from position to position on the image obtained by radiographic imaging due to structural objects included in the subject, such as the type of bone or organ of the subject, the presence or absence of a cavity in an organ, etc., and spatial positions of the structural objects. By obtaining the characteristics information of the subject image Ik as the characteristics information of the virtual model M, and appropriately selecting the parameter used to generate the estimated primary ray image and the estimated scattered ray image depending on the structural object which is (virtually) included at each position of the virtual model M, errors in the primary ray component and the scattered ray component due to the structural objects can be reduced to generate the estimated primary ray image Ip and the estimated scattered ray image Is with higher accuracy.

It should be noted that the value of the parameter $\theta_{x',y'}$ of $K_s$ in the equation (3) may also be changed for each structural object, so that different values of $\theta_{x',y'}$ are applied to different positions depending on the structural object at each position. Further, a three-dimensional image, such as a CT image or MRI image, that is obtained by imaging the same subject K as that of the subject image Ik may be obtained, and the characteristics information of the subject image Ik may be measured and obtained from the CT image or MRI image. In the case where the characteristics information is obtained using a three-dimensional image of the same subject K, accurate information about spatial positions of organs and bones, etc., can be obtained.

Further, any of various methods that can generate the estimated primary ray image Ip and the estimated scattered ray image Is may be used. For example, in place of the equations (2) and (3), for example, a Monte-Carlo simulation method, as taught in H. Kato, "A New Method for Eliminating Scatter Components from a Digital X-ray Image by Later Processing", Journal of Japanese Society of Radiological Technology, Vol. 62, No. 9, pp. 1359-1368, 2006, may be used to generate the estimated primary ray image Ip and the estimated scattered ray image Is. In the case where the Monte-Carlo simulation method is used, it is preferred that the characteristics information used be about structural objects included in the virtual model M, locations of the structural objects, and characteristics of the structural objects to radiation. In this case, the estimated primary ray image Ip and the estimated scattered ray image Is can be generated with higher accuracy.

Further, it is preferred that the modifying unit 34 select, according to the obtained imaging condition, a parameter (such as $\theta_{x',y'}$ in the equations (7) and (8) above), which varies depending on the imaging condition, used to generate the estimated image Im, and perform the operation (S06) to modify the body thickness distribution of the estimated image Im using the selected parameter. This allows setting, according to the imaging condition of the subject image Ik, an appropriate parameter which varies depending on the imaging condition to generate the estimated image Im, thereby allowing more accurately estimating and generating the estimated image Im. As a result, the body thickness distribution of the subject K can be determined with higher accuracy.

Further, the image processing unit 39 which obtains the processed image by performing image processing on the subject image using process parameters depending on the determined body thickness distribution of the subject, and the display control unit 40 which displays the processed image on the display unit are provided. In the case where the judging unit 36A executes the first control and necessary operations are performed to display the processed image, the processed image having higher quality suitable for observation can be provided according to the second termination condition to help image observation by the user. On the other hand, in the case where the judging unit 36A executes the second control and necessary operations are performed to display the processed image, the processed image having high quality can be provided within an acceptable range of time for the user according to the second termination condition to help image observation by the user.

In a case of emergency or when it is desired to check whether or not it is necessary to retake the image, one may desire to once calculate a second body thickness distribution and display a processed image which is generated using the second body thickness distribution, and then calculate a first body thickness distribution, as necessary, and display a processed image which is generated using the first body thickness distribution. In this case, for example, the body thickness distribution determining unit 36 first iteratively executes the body thickness distribution modifying process until the second termination condition is satisfied (by executing the second control) based on the judgment condition, and determines the body thickness distribution (the second body thickness distribution) of the subject image Ik according to the second termination condition. Subsequently, based on the judgment condition, the body thickness distribution determining unit 36 iteratively executes the body thickness distribution modifying process until the first termination condition is satisfied (by executing the first control), and determines the body thickness distribution of the subject image Ik according to the first termination condition. Then, the image processing unit 39 first performs necessary image processing on the subject image using the second body thickness distribution that is obtained earlier to generate the processed image, and the display control unit 40 displays the processed image on the display unit 44. Thereafter, the image processing unit 39 performs necessary image processing on the subject image using the first body thickness distribution that is obtained later to generate the processed image, and the display control unit 40 displays the processed image that is obtained using the first body thickness distribution on the display unit 44.

In the case where the processed image that is generated using the second body thickness distribution is displayed first, the user can possibly roughly understand the part to be noted in the subject image, whether or not the imaging condition of radiographic imaging applied to the subject image is appropriate, etc., and this improves efficiency of image observation by the user and can provide information that is useful for image observation by the user. Thereafter, by displaying the processed image that is generated using the first body thickness distribution, the processed image suitable for image observation can be provided. It should be noted that, in the above-described case, the scattered ray information obtaining unit 37 may perform the operation to obtain the scattered ray information and the scattered ray removing unit 38 may perform the scattered ray removal on the subject image Ik, as necessary. Then, the image processing unit 39 may generate the processed image by performing the necessary image processing on the subject image having been subjected to the scattered ray removal, using the first body thickness distribution (or the second body thickness distribution), and the display control unit 40 may display the first processed image (or the second processed image) on the display unit 44.

In the above-described embodiments, a display or a sound may be used to notify the user with which of the first and the second controls is executed. For example, when the second control is executed, a display to the effect that the image is generated with the simple-type body thickness distribution estimation may be displayed together with the processed image. Alternatively, when the second control is executed, the subject image Ik (the unprocessed image) may be once stored, and the body thickness distribution may be obtained later by executing the first control.

In the above-described embodiments, the operation to obtain the subject image Ik in step S01 shown in FIG. 6 may performed at any timing before the determination in step S04 as to the difference between the subject image and the estimated image.

In the above-described embodiments, the scattered ray information obtaining unit 37 and the scattered ray removing unit 38 in the image analyzing unit 30 may be omitted, so that the operation to obtain the scattered ray information and the operation of scattered ray removal may not be performed by the image analyzing unit 30. In this case, the determined body thickness distribution Tk of the subject K may be outputted to a different device, and the image processing of the subject image Ik and the operation to determine the imaging condition of the subject image Ik may be performed at the different device using the body thickness distribution Tk.

It should be noted that the above-described embodiments are not intended to limit the invention. The body thickness distribution of the subject obtained according to the disclosure can be used with any operation for determining an image processing condition of the subject image depending on the body thicknesses of the subject. For example, the body thickness distribution obtained according to the disclosure may be used to perform gradation processing of density or contrast, noise suppression, dynamic range adjustment, frequency emphasis, etc., of the subject image, which may be a still image or a moving image. Further, the body thickness distribution obtained according to the disclosure can be used with any operation for determining an imaging condition of the subject image depending on the body thickness. In the case where the body thickness distribution obtained according to the disclosure is used to determine the image processing condition or imaging condition, the accurate body thickness distribution applied to the subject image allows enhancing the effect of improving the image quality provided by the determined image processing condition or imaging condition.

The above-described embodiments are only examples, and should not be construed to limit the technical scope of the disclosure. The aspects of the disclosure are not limited to the above-described embodiments, and encompass any combination of any features of the embodiments, as well as various modifications conceivable by those skilled in the art. That is, various additions, changes, and partial removal may be made without departing from the spirit and scope of the disclosure which are derived from the appended claims and equivalents thereof.

Further, various modifications made to the system configuration, the hardware configuration, the flow of the process, the modular configuration, the user interface, the specific contents of operations, etc., in the above-described embodiments without departing from the spirit and scope of the disclosure are also within the technical scope of the disclosure. For example, all or some of the components of the image analyzing device may be implemented by one workstation, or may be implemented by one or more workstations, a server, and a storing unit which are connected via a network.

While the scattered ray removal is performed using a radiographic image obtained by the imaging unit 10 that obtains a radiographic image of the subject using the radiation detector 14 in the above-described embodiments, the disclosure is applicable to a radiographic image that is obtained by photoelectrically reading radiographic image information of the subject which is recorded on a storage phosphor sheet serving as the radiation detector, as taught in Japanese Unexamined Patent Publication Nos. 8(1996)-266529 and 9(1997)-024039, etc.

What is claimed is:
1. A radiographic image analyzing device for analyzing a subject image obtained by radiographic imaging of a subject to estimate a body thickness distribution of the subject, the device comprising:
   an image obtaining unit for obtaining the subject image;
   a body thickness distribution modifying unit for receiving input of a virtual model having an estimated body thickness distribution and modifying the estimated body thickness distribution of the virtual model to output the modified estimated body thickness distribution, the body thickness distribution modifying unit comprising:
  a virtual model obtaining unit for obtaining the inputted virtual model having the estimated body thickness distribution,
  an estimated image generating unit for generating an estimated image, which is an estimate of a radiographic image that would be obtained by radiographic imaging of the subject, by combining an estimated primary ray image, which is an estimate of a primary ray image that would be obtained by radiographic imaging of the obtained virtual model, and an estimated scattered ray image, which is an estimate of a scattered ray image that would be obtained by radiographic imaging of the virtual model, and
  a modifying unit for modifying the obtained estimated body thickness distribution such that a difference between the estimated image and the subject image is reduced, and outputting the modified estimated body thickness distribution; and
  a body thickness distribution determining unit for controlling execution of a body thickness distribution modifying process that causes the modifying unit to modify the estimated body thickness distribution of the virtual model and output the modified estimated body thickness distribution, causes the virtual model obtaining unit to obtain the virtual model having the outputted estimated body thickness distribution inputted thereto, and causes the estimated image generating unit to generate the estimated image from the virtual model, wherein the body thickness distribution modifying process is iteratively executed until a termination condition is satisfied, and, if the termination condition is satisfied, the body thickness distribution determining unit determines the estimated body thickness distribution that is outputted by the body thickness distribution modifying process when the termination condition is satisfied to be used as the body thickness distribution of the subject,
  wherein the body thickness distribution determining unit comprises a judging unit for switching, according to a judgment condition, between a first control under which the body thickness distribution modifying process is iteratively executed until a first termination condition is satisfied and a second control under which the body thickness distribution modifying process is iteratively executed until a second termination condition that is different from the first termination condition is satisfied so that one of the first control and the second control is executed, the number of iterations of the body thickness distribution modifying process under the second control being smaller than the number of iterations of the body thickness distribution modifying process under the first control.

2. The radiographic image analyzing device as claimed in claim 1, wherein the judging unit estimates an estimated run time, which is an estimate of a sum of run times of the body thickness distribution modifying process that is iteratively executed until the first termination condition is satisfied, based on time-series transition of the difference between the estimated image and the subject image during the iteratively executed body thickness distribution modifying process, and the judging unit executes the second control if the estimated run time is greater than a first time limit, and executes the first control if the estimated run time is not greater than the first time limit.

3. The radiographic image analyzing device as claimed in claim 1, wherein, based on processing capacity information that indicates processing capacity of the radiographic image analyzing device, the judging unit executes the second control if the processing capacity is lower than a certain processing level, and executes the first control if the processing capacity is not lower than the certain processing level.

4. The radiographic image analyzing device as claimed in claim 3, wherein the processing capacity information is information indicating the type of the imaging apparatus used to take the subject image.

5. The radiographic image analyzing device as claimed in claim 1, wherein, based on associating information that associates each imaging location with the first control or the second control, the judging unit executes the first control if the imaging location of the subject image is associated with the first control, and executes the second control if the imaging location of the subject image is associated with the second control.

6. The radiographic image analyzing device as claimed in claim 1, wherein, based on emergency display information that indicates whether or not emergency display of the subject image is necessary, the judging unit executes the second control if the emergency display is necessary, and executes the first control if the emergency display is not necessary.

7. The radiographic image analyzing device as claimed in claim 1, wherein, based on associating information that associates each body part shown in the subject image with the first control or the second control, the judging unit executes the first control if the body part shown in the subject image is associated with the first control, and executes the second control if the body part shown in the subject image is associated with the second control.

8. The radiographic image analyzing device as claimed in claim 1, wherein
  the first termination condition represents a first threshold value which is an acceptable value of the difference between the estimated image generated by the estimated image generating unit and the subject image,
  the second termination condition represents a second threshold value which is an acceptable value of the difference between the estimated image generated by the estimated image generating unit and the subject image, and
  the second threshold value is greater than the first threshold value.

9. The radiographic image analyzing device as claimed in claim 1, wherein the second termination condition represents an upper limit value of the number of iterations of the body thickness distribution modifying process, or an upper limit value of a sum of run times of the body thickness distribution modifying process.

10. The radiographic image analyzing device as claimed in claim 1, further comprising:
  an image processing unit for performing image processing on the subject image using a process parameter depending on the body thickness distribution of the subject to obtain a processed image, and
  a display control unit for displaying the processed image on a display unit.

11. A radiographic image analyzing method to be executed by a radiographic image analyzing device for analyzing a subject image obtained by radiographic imaging of a subject to estimate a body thickness distribution of the subject, the method comprising:

an image obtaining step of obtaining the subject image;
a body thickness distribution modifying step of receiving input of a virtual model having an estimated body thickness distribution and modifying the estimated body thickness distribution of the virtual model to output the modified estimated body thickness distribution, the body thickness distribution modifying step comprising:
a virtual model obtaining step of obtaining the inputted virtual model having the estimated body thickness distribution,
an estimated image generating step of generating an estimated image, which is an estimate of a radiographic image that would be obtained by radiographic imaging of the subject, by combining an estimated primary ray image, which is an estimate of a primary ray image that would be obtained by radiographic imaging of the obtained virtual model, and an estimated scattered ray image, which is an estimate of a scattered ray image that would be obtained by radiographic imaging of the virtual model, and
a modifying step of modifying the obtained estimated body thickness distribution such that a difference between the estimated image and the subject image is reduced, and outputting the modified estimated body thickness distribution; and
a body thickness distribution determining step of controlling execution of a body thickness distribution modifying process that causes the estimated body thickness distribution of the virtual model to be modified and the modified estimated body thickness distribution to be outputted in the modifying step, causes the virtual model having the outputted estimated body thickness distribution to be obtained in the virtual model obtaining step, and causes the estimated image to be generated from the virtual model in the estimated image generating step, wherein the body thickness distribution modifying process is iteratively executed until a termination condition is satisfied, and, if the termination condition is satisfied, the estimated body thickness distribution that is outputted by the body thickness distribution modifying process when the termination condition is satisfied is determined to be used as the body thickness distribution of the subject,
wherein the body thickness distribution determining step comprises a judging step of switching, according to a judgment condition, between a first control under which the body thickness distribution modifying process is iteratively executed until a first termination condition is satisfied and a second control under which the body thickness distribution modifying process is iteratively executed until a second termination condition that is different from the first termination condition is satisfied so that one of the first control and the second control is executed, the number of iterations of the body thickness distribution modifying process under the second control being smaller than the number of iterations of the body thickness distribution modifying process under the first control.

12. A non-transitory computer-readable recording medium containing a radiographic image analyzing program for analyzing a subject image obtained by radiographic imaging of a subject to estimate a body thickness distribution of the subject, the program causing a computer to function as:
an image obtaining unit for obtaining the subject image;
a body thickness distribution modifying unit for receiving input of a virtual model having an estimated body thickness distribution and modifying the estimated body thickness distribution of the virtual model to output the modified estimated body thickness distribution, the body thickness distribution modifying unit comprising:
a virtual model obtaining unit for obtaining the inputted virtual model having the estimated body thickness distribution,
an estimated image generating unit for generating an estimated image, which is an estimate of a radiographic image that would be obtained by radiographic imaging of the subject, by combining an estimated primary ray image, which is an estimate of a primary ray image that would be obtained by radiographic imaging of the obtained virtual model, and an estimated scattered ray image, which is an estimate of a scattered ray image that would be obtained by radiographic imaging of the virtual model, and
a modifying unit for modifying the obtained estimated body thickness distribution such that a difference between the estimated image and the subject image is reduced, and outputting the modified estimated body thickness distribution; and
a body thickness distribution determining unit for controlling execution of a body thickness distribution modifying process that causes the modifying unit to modify the estimated body thickness distribution of the virtual model and output the modified estimated body thickness distribution, causes the virtual model obtaining unit to obtain the virtual model having the outputted estimated body thickness distribution inputted thereto, and causes the estimated image generating unit to generate the estimated image from the virtual model, wherein the body thickness distribution modifying process is iteratively executed until a termination condition is satisfied, and, if the termination condition is satisfied, the body thickness distribution determining unit determines the estimated body thickness distribution that is outputted by the body thickness distribution modifying process when the termination condition is satisfied to be used as the body thickness distribution of the subject,
wherein the body thickness distribution determining unit comprises a judging unit for switching, according to a judgment condition, between a first control under which the body thickness distribution modifying process is iteratively executed until a first termination condition is satisfied and a second control under which the body thickness distribution modifying process is iteratively executed until a second termination condition that is different from the first termination condition is satisfied so that one of the first control and the second control is executed, the number of iterations of the body thickness distribution modifying process under the second control being smaller than the number of iterations of the body thickness distribution modifying process under the first control.

* * * * *